United States Patent [19]

Lösel et al.

[11] Patent Number: 4,766,217

[45] Date of Patent: Aug. 23, 1988

[54] PREPARATION OF 5,6-DIHYDRO-PYRROLO[2,1-A]ISOQUINO-LINES

[75] Inventors: Walter Lösel, Gau-Algesheim; Otto Roos, Schwabenheim; Gerd Schnorrenberger, Ingelheim am Rhein, all of Fed. Rep. of Germany

[73] Assignee: Boehringer Ingelheim KG, Ingelheim am Rhein, Fed. Rep. of Germany

[21] Appl. No.: 62,851

[22] Filed: Jun. 16, 1987

Related U.S. Application Data

[60] Division of Ser. No. 843,084, Mar. 24, 1986, Pat. No. 4,694,085, which is a continuation-in-part of Ser. No. 691,444, Jan. 14, 1985, abandoned.

[51] Int. Cl.$^4$ ............... C07D 401/02; C07D 491/147; C07D 471/04
[52] U.S. Cl. .......................................... 546/94; 546/65
[58] Field of Search ........................... 546/94, 65

[56] References Cited

U.S. PATENT DOCUMENTS 4,652,567 3/1987 Martin et al. .................... 546/94

Primary Examiner—Henry R. Jiles
Assistant Examiner—J. Richter
Attorney, Agent, or Firm—Weissenberger, Hammond & Littell

[57] ABSTRACT

5,6,-dihydro-pyrrolo[2,1-a]isoquinolines of the formula

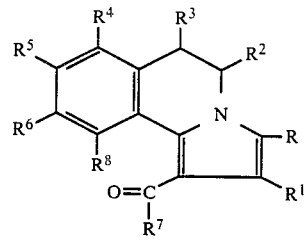

are prepared by heating a 1-(3-furyl)-3,4-dihydro-isoquinoline of the formula

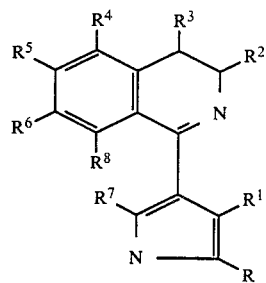

in a primary or secondary amine to at least 80° C. for several hours, the amine is removed, the reaction product is treated with dilute acid, and the reaction product is purified and isolated.

4 Claims, No Drawings

PREPARATION OF 5,6-DIHYDRO-PYRROLO[2,1-A]ISOQUINOLINES

CROSS-REFERENCE TO RELATED APPLICATION

This is a division of copending application Ser. No. 843,084, filed Mar. 24, 1986, now U.S. Pat. No. 4,694,085; which in turn is a continuation-in-part of application Ser. No. 691,444, filed Jan. 14, 1985, now abandoned.

FIELD OF THE INVENTION

This invention relates to novel compounds. More particularly, this invention relates to 5,6-dihydropyrrolo[2,1-a]isoquinolines and the preparation thereof.

BACKGROUND OF THE INVENTION

Various derivatives of 5,6-dihydro-pyrrolo[2,1-a]isoquinoline have a number of valuable pharmacological properties [(C. Casagrande, A. Invernizzi, R.-Ferrini, and G. G. Ferrari, J. Med. Chem. 11, 765, 1968; C. Casagrande, A. Invernizzi, R. Ferrini, and G. Miracoli, Farmaco, Ed. Sci. 27, (12), 1029–1044 (1972); S. A. Siphar, (Erf. G. Ferrari and C. Casagrande), Brit. Pat. No. 1,153,670 (5/29/69) (Chem. Abstr. 71, 81215g); N. Nakayama, N. Imamura, T. Kanazawa, and S. Yoneda, Heterocycles 20, (1), 168 (1983)]. In spite of their pharmacological importance, this group of compounds has hitherto been used only to a small extent due to the inadequate methods of synthesis.

In the majority of syntheses known in the literature, the tricycle is closed by reacting tautomerizable 1-alkyl-3,4-dihydroisoquinolines with 1,2-biselectrophiles. [C. Casagrande, A. Invernizzi, R. Ferrini, and G. G. Ferrari, J. Med. Chem. 11, 765, 1968; J. Thesing and H. F. Funk, Chem. Ber. 19, 1546–1551 (1958); Y. Ban and M. Terashima, Chem. Pharm. Bull. 13 (7) 775–785 (1965); S. Sakai, A. Kubo, M. Inaba, M. Katagiri, and K. Tanna, Yakugaku Zasshi 86 (9), 856–858 (1966) (Chem. Abstr. 65, 18558a (1966)); H. Meyer, Liebigs Ann. Chem. 1981, 1534–1544]. Due to the limited choice of suitable reactors, the functionality of the pyrrole substituents, generally alkyl, aryl, and ester functions, can only be varied within narrow limits. Other methods are used in special cases [N. Nakayama, N. Imamura, T. Kanazawa, and S. Yoneda, Heterocycles 20, (1), 168 (1983); Ph. Cauwel and J. Gardent, Tetrahydron Lett. 1972 (27) 2781–2784; F. M. Hershenson, J. Org. Chem. 1975, 40 (6), 740–743; E. Breuer, S. Zbaida, J. Pesso, and I. Ronen-Braunstein, Tetrahedron 1977, 33 (10), 1145–1148; S. Kano, T. Yokumatsu, Y. Yuasa, and S. Shibuya, Heterocycles, 19, (11), 2143–2145 (1982); W. E. McEwen, I. C. Wang Huang, C. P. Cartaya Marin, F. McCarty, E. Marmugi Segnini, Ch. M. Zepp III, and J. J. Lubinkowski, J. Org. Chem. 1982, 47, 3098–3105] are interesting only for their reaction mechanisms [M. Hanaoka, A. Wada, Y. Sakamoto, M. Ichihara, S. Yasuda, and T. Imanishi, Heterocycles 16, (11), 1933–1936 (1981); G. Blasko, G. Dörnyei, M. Barczai-Beke, P. Pechy, and C. Szantay, Heterocycles 20, (2), 273–278 (1983)].

DESCRIPTION OF THE INVENTION

The present invention provides a simple and effective method of preparing new 5,6-dihydro-pyrrolo[2,1-a]isoquinolines by base-catalyzed rearrangement of the 1-(3-furyl)-3,4-dihydroisoquinolines which are known from German Offenlegungsschrift No. 31 43 876 and are readily accessible. More specifically, the invention relates to 5,6-dihydro-pyrrolo[2,1-a]isoquinolines of the formula

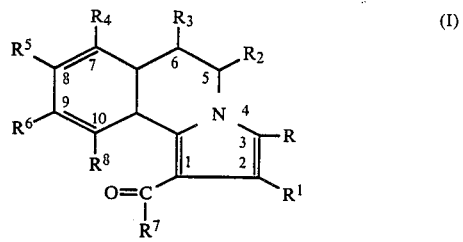

wherein

R, $R^2$, $R^3$, and $R^7$, which may be identical or different, each represent a hydrogen atom or an alkyl group having from 1 to 4 carbon atoms;

$R^1$ represents a cyano, hydroxycarbonyl, or alkoxycarbonyl group with 1 to 4 carbon atoms or a primary or secondary, substituted or unsubstituted, aliphatic, cycloaliphatic, araliphatic, aromatic, or heterocyclic aminocarbonyl group;

$R^4$, $R^8$, which may be identical or different, each represent a hydrogen atom or a hydroxyl, alkoxy or alkylthio with up to 4 carbon atoms, or an $NR^9R^{10}$ group;

$R^5$ and $R^6$, which may be identical or different, each represent a hydroxyl group or an alkoxy or alkylthio group having from 1 to 4 carbon atoms, or together represent an $-O-CH_2-O-$, $-O-CH_2-CH_2-O-$, or $-O-CH=CH-O-$ group;

$R^9$ represents a hydrogen atom or an alkyl group having from 1 to 4 carbon atoms; and $R^{10}$ represents an alkyl group having from 1 to 4 carbon atoms, optionally substituted by a hydroxyl, methoxy, or furfuryl group, and a process for preparing them. The process is characterized in that a 1-(3-furyl)-3,4-dihydro-isoquinoline of the formula

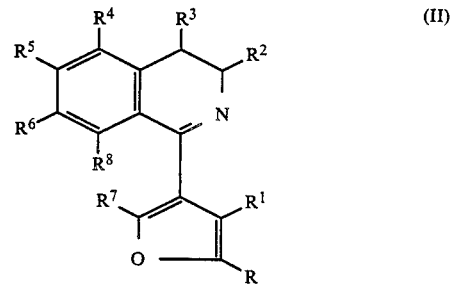

wherein R and $R^1$ to $R^8$ are as hereinbefore defined, is heated in a primary or secondary amine to at least 80° C. for several hours, the amine is removed, the reaction product is treated with dilute acid, and the reaction product is purified and isolated.

Suitable amines include primary and secondary aliphatic, cycloaliphatic, and araliphatic amines. The preferred amines are morpholine, piperidine, 2-(3,4-dimethoxyphenyl)-ethylamine, 1-amino-2-propanol, and methoxy-ethylamine.

During the working up, the reaction product is normally treated with acids, preferably dilute inorganic acids, in order to cleave any azomethines formed and eliminate the last traces of the amine from the reaction product.

The length of the reaction depends upon the reaction temperature. At temperatures of about 100° C., reaction times of up to 16 hours are required. At temperatures of 200° C., a reaction time of 1 to 2 hours is sufficient. If higher boiling primary or secondary amines are used, it is sufficient to reflux the starting compound in the amine as solvent. In the case of lower boiling amines, the reaction may also be carried out in a closed system, e.g., in an autoclave or a bomb tube.

After the reaction mixture has been worked up, the end compounds are obtained in yields of from 70 to 98%, and according to elementary analysis and mass spectrum these compounds are isomeric with respect to the starting compounds of Formula II. The end compounds of Formula I normally occur as products which are pure by NMR spectroscopy.

Under the conditions of rearrangement chosen, the ester functions are normally maintained even when primary amines are used and there is no conversion into corresponding amides.

The rearrangement of the 1-(3-furyl)-3,4-dihydro-isoquinolines of Formula II into the 5,6-dihydro-pyrrolo[2,1-a]isoquinolines of Formula I is noticeable in the $^1$H-MNR spectra, particularly in the disappearance of the proton signals of the furan system. For the free bases of the starting compounds of Formula II, the two doublets (J=1.5 Hz) are between δ=7.58 and δ=8.01 ppm, while those for the corresponding hydrochlorides are in the region from δ=8.20–8.68 ppm.

In their place, new proton resonances appear in the rearrangement products of Formula I at δ=6.70–6.87 ppm and δ=9.09–10.67 ppm, and according to their form and position they must be associated with the proton [3-H] in the pyrrolo ring and an aldehyde proton in compounds of Formula I wherein $R^7$ represents hydrogen. As a further expression of the thorough change in structure as the compounds of Formula II make their transition into the end products of Formula I, there is a marked low field shift of the aromatic proton [10-H]. This correlation arises from the considerable dependency of the chemical shift value of this signal upon the substitution at C-1, which proves the spatially close placing of the two functions.

The structure of the end compound can, furthermore, be guaranteed irrespective of the spectroscopic findings by means of the secondary products. The 5,6-dihydro-pyrrolo[2,1-a]isoquinolines of Formula I have, in the pyrrolo ring, a keto or aldehyde carbonyl function and a carboxylic acid carbonyl function which can be converted in many ways.

The conversion of 1-(3-furyl)-3,4-dihydro-isoquinolines into the 5,6-dihydro-pyrrolo[2,1-a]isoquinolines of Formula I according to the invention provides a new means of access, which is preparatively simple, to this type of substance. The advantage of this process is the possibility of introducing functional groups regioselectively into the pyrrolo ring.

The novel 5,6-dihydro-pyrrolo[2,1-a]isoquinolines of Formula I which may be prepared using the process of the invention are valuable starting compounds for the preparation of pharmaceutically active pyridazino[4',5':3,4]pyrrolo[2,1-a]-3,4,11,12-tetrahydroisoquinolines of the formula

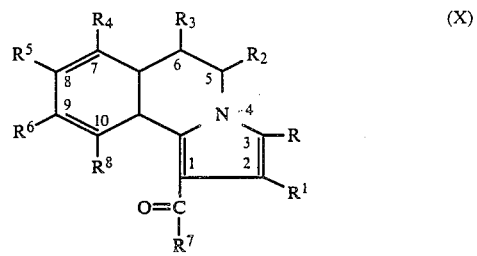

wherein R and $R^2$ to $R^8$ are as described above and $R^9$ and $R^{10}$, which may be the same or different, are each, for example, hydrogen or an alkyl group having from 1 to 5 carbon atoms, a di-($C_1$-$C_2$)alkylamino-($C_1$-$C_5$)alkyl group, a cycloalkyl group having from 3 to 7 carbon atoms, or a phenyl group optionally substituted by one or more halogen, alkyl having one or two carbon atoms, or alkoxy having one or two carbon atoms, or $R^9$ and $R^{10}$ together with the nitrogen atom may form a from 3- to 7-member heterocyclic ring optionally containing an oxygen atom or an additional nitrogen atom as a ring heteroatom. The compounds of Formula X have muscarin-agonistic, calcium-antagonistic, antihypoxiedotic, nootropic, cardiac, metabolic, and hypotensive effects.

Examples of compounds of Formula X include the following:

3,4-Dihydro-6,7-dimethoxy-12-N,N-dimethylaminoethylaminopyridazino[4',5':3,4]pyrrolo[2,1-a]isoquinoline hydrochloride;

3,4-Dihydro-6,7-dimethoxy-12-hydrazino-pyridazino[4',5':3,4]pyrrolo[2,1-a]isoquinoline;

3,4-Dihydro-6,7-dimethoxy-12-dimethylamino-pyridazino[4',5':3,4]pyrrolo[2,1-a]isoquinoline hydrochloride;

3,4-Dihydro-6,7-dimethoxy-12-morpholino-pyridazino[4',5':3,4]pyrrolo[2,1-a]isoquinoline hydrochloride;

3,4-Dihydro-6,7-dimethoxy-pyridazino[4',5':3,4]pyrrolo[2,1-a]isoquinolin-12-acetonylhydrazone;

3,4-Dihydro-6,7-dimethoxy-12-anilino-pyridazino[4',5':3,4]pyrrolo[2,1-a]isoquinoline hydrochloride;

3,4-Dihydro-6,7-dimethoxy-12-methylamino-pyridazino[4',5':3,4]pyrrolo[2,1-a]isoquinoline hydrochloride;

3,4-Dihydro-6,7-dimethoxy-12-ethylamino-pyridazino[4',5':3,4]pyrrolo[2,1-a]isoquinoline hydrochloride;

3,4-Dihydro-6,7-dimethoxy-12-diethylamino-pyridazino[4',5':3,4]pyrrolo[2,1-a]isoquinoline hydrochloride;

3,4-Dihydro-6,7-dimethoxy-12-cyclopropylamino-pyridazino[4',5':3,4]pyrrolo[2,1-a]isoquinoline hydrochloride;

3,4-Dihydro-6,7-dimethoxy-12-butylamino-pyridazino[4',5':3,4]pyrrolo[2,1-a]isoquinoline hydrochloride;

3,4-Dihydro-6,7-dimethoxy-12-N,N-dimethylhydrazino-pyridazino[4',5':3,4]pyrrolo[2,1-a]isoquinoline hydrochloride;

3,4-Dihydro-6,7-dimethoxy-12-(2-methoxyethyl)-amino-pyridazino[4',5':3,4]pyrrolo[2,1-a]isoquinoline hydrochloride;

3,4-Dihydro-6,7-dimethoxy-12-[2-(3,4-dimethoxyphenyl)-ethyl]amino-pyridazino[4',5':3,4]pyrrolo[2,1-a]isoquinoline hydrochloride;

3,4-Dihydro-6,7-dimethoxy-12-(3-aminopyrazolyl)-pyridazino[4',5':3,4]pyrrolo[2,1-a]isoquinoline hydrochloride;

3,4-Dihydro-6,7-dimethoxy-12-cyclopentylamino-pyridazino[4',5':3,4]pyrrolo[2,1-a]isoquinoline hydrochloride;

3,4-Dihydro-6,7-dimethoxy-12-cyclohexylmethylamino-pyridazino[4',5':3,4]pyrrolo[2,1-a]isoquinoline hydrochloride 3,4-Dihydro-6,7-dimethoxy-12-propargylamino-pyridazinio[4',5':3,4]pyrrolo[2,1-a]isoquinoline hydrochloride;

3,4-Dihydro-6,7-dimethoxy-12-{2-[2-(1-methyl)-pyrrolidinyl]ethyl}-amino-pyridazino[4',5':3,4]pyrrolo[2,1-a]isoquinoline hydrochloride;

3,4-Dihydro-6,7-dimethoxy-12-[2-(1-piperidinyl)-ethyl]-aminopyridazino[4',5':3,4]pyrrolo[2,1-a]isoquinoline hydrochloride;

3,4-Dihydro-6,7-dimethoxy-12-pyrrolidinyl-pyridazino[4',5':3,4]pyrrolo[2,1-a]isoquinoline hydrochloride;

3,4-Dihydro-6,7-dimethoxy-12-n-propylamino-pyridazino[4',5':3,4]pyrrolo[2,1-a]isoquinoline hydrochloride;

12-Allylamino-3,4-dihydro-6,7-dimethoxy-pyridazino[4',5':3,4]pyrrolo[2,1-a]isoquinoline hydrochloride;

3,4-Dihydro-6,7-dimethoxy-12-[4-(2-methoxyphenyl)-piperazinyl]pyridazino[4',5':3,4]pyrrolo[2,1-a]isoquinoline hydrochloride;

3,4-Dihydro-6,7-dimethoxy-12-(3-dimethylaminopropyl)-aminopyridazino[4',5':3,4]pyrrolo[2,1-a]isoquinoline hydrochloride;

3,4-Dihydro-6,7-dimethoxy-12-[2-(1-morpholinyl)-ethyl]-aminopyridazino[4',5':3,4]pyrrolo[2,1-a]isoquinoline hydrochloride;

3,4-Dihydro-6,7-dimethoxy-12-n-phenylamino-pyridazino[4',5':3,4]pyrrolo[2,1-a]isoquinoline hydrochloride;

3,4-Dihydro-6,7-dimethoxy-12-cyclohexylamino-pyridazino[4',5':3,4]pyrrolo[2,1-a]isoquinoline hydrochloride;

3,4-Dihydro-6,7-dimethoxy-12-[4-(2-phenylethyl)-piperazinyl]pyridazino[4',5':3,4]pyrrolo[2,1-a]isoquinoline hydrochloride;

3,4-Dihydro-6,7-dimethoxy-12-furfurylamino-pyridazino[4',5':3,4]pyrrolo[2,1-a]isoquinoline hydrochloride;

3,4-Dihydro-6,7-dimethoxy-12-(3-methoxypropylamino)-pyridazino[4',5':3,4]pyrrolo[2,1-a]isoquinoline hydrochloride;

3,4-Dihydro-6,7-dimethoxy-12-isopentylamino-pyridazino[4',5':3,4]pyrrolo[2,1-a]isoquinoline hydrochloride;

3,4-Dihydro-6,7-dimethoxy-12-[2-(1-pyrrolidinyl)-ethyl]-aminopyridazino[4',5':3,4]pyrrolo[2,1-a]isoquinoline hydrochloride;

3,4-Dihydro-6,7-dimethoxy-12-(2-hydroxyethyl)-amino-pyridazino[4',5':3,4]pyrrolo[2,1-a]isoquinoline hydrochloride;

3,4-Dihydro-6,7-dimethoxy-12-(4-fluoroanilino)-pyridazino[4',5':3,4]pyrrolo[2,1-a]isoquinoline hydrochloride;

3,4-Dihydro-6,7-dimethoxy-12-[2-(4-pyridinyl)-ethyl]-aminopyridazino[4',5':3,4]pyrrolo[2,1-a]isoquinoline hydrochloride;

3,4-Dihydro-6,7-dimethoxy-12-[2-(2-pyridinyl)-ethyl]-aminopyridazino[4',5':3,4]pyrrolo[2,1-a]isoquinoline hydrochloride;

12-(4-Amino-1-benzyl-piperidinyl)-3,4-dihydro-6,7-dimethoxypyridazino[4',5':3,4]pyrrolo[2,1-a]isoquinoline hydrochloride;

3,4-Dihydro-6,7-dimethoxy-12-[2-(3-thieno)-ethyl]-aminopyridazino[4',5':3,4]pyrrolo[2,1-a]isoquinoline hydrochloride;

3,4-Dihydro-6,7-dimethoxy-12-amino-pyridazino[4',5':3,4]pyrrolo[2,1-a]isoquinoline hydrochloride;

3,4-Dihydro-6,7-dimethoxy-12-[2-[2-(1-methyl)-pyrrolyl]-ethyl]amino-pyridazino[4',5':3,4]pyrrolo[2,1-a]isoquinoline hydrochloride;

3,4-Dihydro-6,7-dimethoxy-12-[4-(2-phenylethyl)-piperazinyl]pyridazino[4',5':3,4]pyrrolo[2,1-a]isoquinoline hydrochloride;

3,4-Dihydro-6,7-dimethoxy-12-isobutylamino-pyridazino[4',5':3,4]pyrrolo[2,1-a]isoquinoline hydrochloride; and 3,4-Dihydro-6,7-dimethoxy-12-benzylamino-pyridazino[4',5':3,4]pyrrolo[2,1-a]isoquinoline hydrochloride.

To obtain a final product of Formula X, a compound of Formula I is reacted in a multistage process. This process can be represented by the following reaction scheme:

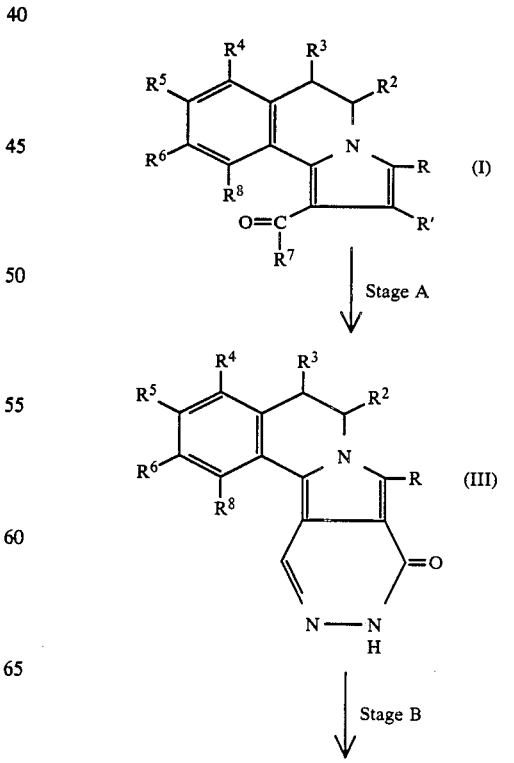

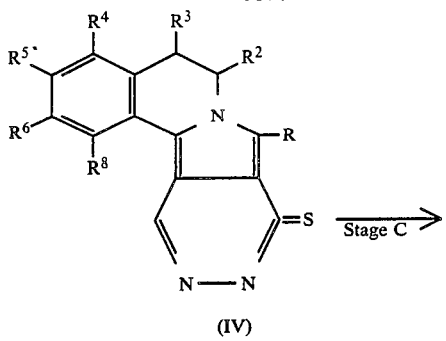

(IV)

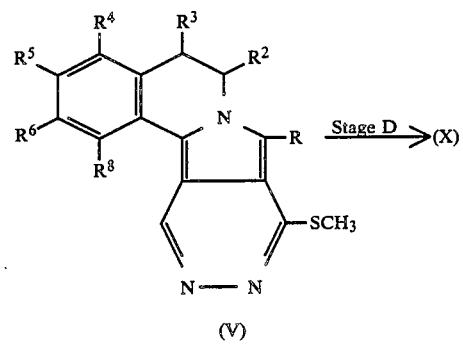

(V)

Stage A is carried out by reacting a compound of Formula I in which R' is, e.g., ($C_1$–$C_4$)alkoxycarbonyl with hydrazinhydrate, to yield Compound III.

Stage B is carried out by conversion of Compound III to the thio derivative of Formula IV by reaction with phosphorpentasulfide.

Stage C is effected by reaction of the thio compound of Formula IV with dimethylacetamide and methyliodide.

Stage D is carried out by reaction of the methylthio compound of Formula V with an amine of formula HNR$^9$R$^{10}$ in a high boiling point solvent, e.g., dimethylformamide and dimethylacetamide. The reaction can be carried out under reflux and may require from 1 to 15 hours, dependent upon the reactants used.

In tests carried out on isolated guinea-pig atria, the compounds of Formula X demonstrate good cardiotonic activity. Such tests were carried out according to the protocol of R. Reichl, W. Traunecker, A. Engelhardt: Proceedings of the 12th Meeting of the European Society for the Study of Drug Toxicity, Uppsala, June 1970, Excerpta Medica Int. Congr. Series NR. 220- Isolated Atrium.

The compounds of formula X also demonstrate a strong binding to muscarinic receptors as demonstrated by tests in which homogenate from various sections of rat brain were incubated with tritium-M-methyl-scopolamine and thereafter compounds according to Formula X were added, leading to displacement of the ligand. The amount of ligand displaced is a measure of the affinity of the substance for the muscarincholinergen receptors. (M. Watson et al., *Live Science*, Vol. 32, pages 3001–3011 (1983), and R. Hammer et al., *Nature*, Vol. 283, pages 90–92 (1980)).

On the basis of these findings, the compounds of Formula X and their acid addition salts are potentially suitable for use in the treatment of cerebral metabolic disturbances. Suggested oral dosages are from about 5 to 500 mg (from about 0.067 to 6.7 mg/kg) per dose, preferably from about 20 to 250 mg (from about 0.27 to 3.3 mg/kg) per dose, and suggested parenteral dosages are from about 0.5 to 150 mg (from about 0.0067 to 2.0 mg/kg) per dose, preferably from about 5 to 50 mg (from about 0.067 to 0.67 mg/kg) per dose.

The following examples are intended to illustrate the invention and should not be construed as limiting the invention thereto.

EXAMPLES

Melting points: apparatus according to Tottoli (Messrs. Büchi), not corrected. Elementary analyses: microanalytical laboratory of Boehringer· Ingelheim KG. IR spectra: Perkin-Elmer 257 (in Nujol; intensity data: s=strong, m=medium, w=weak, br=broad). 1H-(90 MHz)-spectra: Bruker WH 90, tetramethylsilane as the internal standard; δ=values). Mass spectra: Varian MAT-CH 7 (70 eV; direct inlet conditions; evaporation temperature about 200° C.). Thin layer chromatography (TLC): ready-made TLC plates, silica gel F$_{254}$ (Merck): eluant systems methylene chloride/methanol (100:10).

The 3-[3,4-dihydro-isoquinolinyl(1)]-furan-4-carboxylic acid derivatives required as starting compounds of Formula II may be prepared according to the data in DE-OS No. 31 43 876, incorporated herein by reference.

1-FORMYL-5,6-DIHYDRO-PYRROLO[2,1-a]ISOQUINOLINE-2-CARBOXYLIC ACID DERIVATIVES

General method

Fifty mmols of the 1-(3-furyl)-3,4-dihydro-isoquinoline of Formula II are stirred, with N$_2$ protection, in 25 ml of the freshly distilled amine specified for 1 to 2 hours at boiling temperature. After the reaction has ended, the mixture is evaporated to dryness in vacuo, the residue is dissolved in methylene chloride, washed successively with dilute hydrochloric acid and water, and then dried and evaporated. The residue is triturated with ethyl acetate and subjected to suction filtration. The crude products, which are uniform according to NMR spectroscopy, can be processed without further purification. For analysis, samples of the reaction products are purified by column chromatography [silica gel; methylene chloride/methanol (100:2)] and then crystallized from the solvents specified.

Example 1

Ethyl 1-formyl-5,6-dihydro-8,9-dimethoxy-pyrrolo[2,1-a]isoquinoline-2-carboxylate Prepared by rearrangement of ethyl 3-[3,4-dihydro-6,7-dimethoxy-isoquinolyl-(1)]-furan-4-carboxylate with morpholine.

Yield: 98%; melting point: 185°–187° C. (from ethyl acetate)

IR: 3110 w (CH), 3060 w (CH), 1730 sh, 1700 s (CHO), 1655 s (COOR) 1600 m, 1570 m cm$^{-1}$.

$^1$H-NMR (CD$_3$OD): δ=1.37 (t, J=7 Hz; 3H, CH$_3$—CH$_2$), 3.00 (t, J=7 Hz; 2H, Ar—CH$_2$), 3.91, 4.01 in each case (s, 3H, OCH$_3$), 4.07 (t, J=7 Hz); 2H, CH$_2$—CH$_2$—N), 6.71 (s, 1H, 3-H), 7.33 (s, 1H, 7-H), 8.62 (s, 1H, 10-H), 10.67 (s, 1H, CHO). MS: m/z=329 (100%, M+), 300 (41%, M—CHO), 283 (M—C$_2$H$_5$OH).

C$_{18}$H$_{19}$NO$_5$ (329.35) Calculated: C. 65.64, H. 5.81, N. 4.25; Found: 65.93, 6.01, 4.00.

Example 2

Ethyl 1-formyl-5,6-dihydro-8-methoxy-9-hydroxy-pyrrolo[2,1-a]isoquinoline-2-carboxylate Prepared by rearrangment of ethyl 3-[3,4-dihydro-6-methoxy-7-hydroxy-isoquinolinyl-(1)]-furan-4-carboxylate with morpholine.

Yield: 68%; melting point: 218°–222° C. (from ethyl acetate)

IR: 3400–3100 m br (OH), 3070 w, 1700 s (CHO), 1640 s (COOR), 1600 s, 1590 s, 1530 s, cm$^{-1}$.

$^1$H-NMR (CDCl$_3$): δ=1.36 (t, J=7 Hz; 3H, C$\underline{H}_3$—CH$_2$), 2.98 (t, J=7 Hz; 2H, Ar—C$\underline{H}_2$), 3.99 (s, 3H, OCH$_3$), 4.04 (t, J=7 Hz; 2H, C$\underline{H}_2$—CH$_2$—N), 4.33 (q, J=7 Hz; 2H, CH$_3$—C$\underline{H}_2$), 5.73 (s, broad, 1H, OH), 6.72 (s, 1H, 3-H), 7.34 (s, 1H, 7-H), 8.36 (s, 1H, 10-H), 10.66 (s, 1H, CHO).

C$_{17}$H$_{17}$NO$_5$ (315.33) Calculated: C. 64.75, H. 5.43, N. 4.44; Found: 64.94, 5.52, 4.19.

Example 3

Ethyl 1-formyl-5,6-dihydro-8,9-dioxymethylene-pyrrolo[2,1-a]isoquinoline-2-carboxylate Prepared by rearrangement of ethyl 3-[3,4-dihydro-6,7-dioxymethylene-isoquinolyl-(1)]-furan-4-carboxylate hydrochloride with 2-(3,4-dimethoxyphenyl)-ethylamine.

Yield: 73%; melting point: 167°–168° C. (from ethyl acetate).

IR: 3125 m, 1690 s (CHO), 1660 s (COOR), 1620 w cm$^{-1}$.

$^1$H-NMR (CDCl$_3$): δ=1.36 (t, J=7 Hz; 3H, C$\underline{H}_3$—CH$_2$), 2.98 (t, J=6.5 Hz; 2H, Ar—C$\underline{H}_2$), 4.05 (t, J=6.5 Hz; 2H, C$\underline{H}_2$—CH$_2$—N), 4.32 (q, J=7 Hz; 2H, CH$_3$—C$\underline{H}_2$), 5.98 (s, 2H, O—CH$_2$—O), 6.70 (s, 1H, 3-H), 7.34 (s, 1H, 7-H), 8.32 (s, 1H, 10-H), 10.66 (s, 1H, CHO)

C$_{17}$H$_{15}$NO$_5$ (313.31) Calculated: C. 65.17. H. 4.83, N. 4.47; Found: 65.33, 4.96, 4.41.

Example 4

1-Formyl-5,6-dihydro-8,9-dimethoxy-pyrrolo[2,1-a]isoquinoline-2-carbonitrile (a) Prepared by rearrangement of 3-[3,4-dihydro-6,7-dimethoxy-isoquinolinyl-(1)]-furan-4-carbonitrile hydrochloride with morpholine.

Yield: 83%; melting point: 221°–222° C. (from ethyl acetate).

IR: 3100 w (CH), 2220 s (CN), 1660 s (CHO), 1600 m, 1575 m cm$^{-1}$.

$^1$H-NMR (CDCl$_3$): δ=3.06 (t, J=7 Hz; 2H, Ar—C$\underline{H}_2$), 3.91, 3.98 in each case (s, 3H, OCH$_3$), 4.11 (t, J=7 Hz; 2H, CH$_2$—C$\underline{H}_2$—N), 6.76 (s, 1H, 3-H), 7.20 (s, 1H, 7-H), 8.10 (s, 1H, 10-H), 10.14 (s, 1H, CHO).

MS: m/z-282 (100%, M$^+$), 267 (19%, M—CH$_3$), 239 (9%, M—CH$_3$—CO).

C$_{16}$H$_{14}$N$_2$O$_3$ (282.30) Calculated: C. 68.07, H. 5.00, N. 9.92; Found: 68.07, 5.12, 9.83.

(b) Prepared by rearrangement in dimethylformamide (DMF). Fourteen grams (43.92 mmol) of the starting compound of Formula II were heated to boiling in 200 ml of pure DMF for 45 minutes. Then the solvent was eliminated in vacuo, and the residue was distributed between methylene chloride and water, dried over sodium sulfate, purified on silica gel [eluant: methylene chloride/methanol (100:5)], and crystallized from ethyl acetate (bright orange crystals). According to its melting point of 220°–221° C., IR and NMR spectra, elementary analysis, and chromatography, the reaction product is identical to the end product prepared in (a).

C$_{16}$H$_{14}$N$_2$O$_3$ (282.30) Calculated: C. 68.07, H. 5.00, N. 9.92; Found: 68.19, 5.12, 9.92.

Example 5

1-Formyl-5,6-dihydro-8,9-dimethoxy-pyrrolo[2,1-a]isoquinoline-2-carboxylic acid-(2-hydroxypropyl)-amide Prepared by rearrangement of 3-[3,4-dihydro-6,7-dimethoxyisoquinolinyl-(1)]-furane-4-carboxylic acid-(2-hydroxypropyl)amide with morpholine.

Yield: 67%; M.p.: 196°–197° C. (from ethanol/ether).

IR: 3260–3140 m, 3060 m, 1650 sh, 1640 sh, 1630 s (CO), 1600 s, 1570 s cm$^{-1}$.

$^1$H-NMR (CDCl$_3$): δ=1.26 (t, J=7 Hz; 3H, C$\underline{H}_3$—CH$_2$), 3.03 (t, J=6.5 Hz; 2H, Ar—C$\underline{H}_2$), 3.33–3.67 (m, 3H, C$\underline{H}_2$—C$\underline{H}$), 3.86 (s, 7H, 2×OCH$_3$ and 1 OH), 4.08 (t, J=6.5 Hz; 2H, CH$_2$—C$\underline{H}_2$—N), 6.87 (s, 1H, 3-H), 7.08 (s, 1H, 7-H), 7.62 (s, 1H, 10-H), 10.17 (s, 1H, CHO), 10.38 (t, J=5 Hz; 1H, N$\underline{H}$CO).

C$_{19}$H$_{22}$N$_2$O$_5$ (358.40). Calculated: C. 63.67, H. 6.18, N. 7.82; Found: 63.59, 6.11, 7.81.

Example 6

1-Formyl-5,6-dihydro-8,9-dimethoxy-pyrrolo[2,1-a]isoquinoline-2-carboxylic acid-(2-furfuryl)-amide Prepared by rearrangement of 3-[3,4-dihydro-6,7-dimethoxyisoquinolinyl-(1)]-furan-4-carboxylic acid-(2-furfuryl)-amide hydrochloride with morpholine.

Yield: 78%; reddish-orange crystals; melting point: 194°–195° C. (from methylene chloride/ether).

IR: 3600–3250 m br (NH), 3080 w, 3060 m, 1670 sh, 1650 s (CO), 1600 m, 1560 s cm$^{-1}$.

$^1$H-NMR (CDCl$_3$): δ=2.89 (t, J=6.5 Hz; 2H, Ar—C$\underline{H}_2$), 3.84 (t, J=6.5 Hz; 2H, CH$_2$—C$\underline{H}_2$—N), 3.83, 3.91 in each case (s, 3H, OCH$_3$), 4.68 (s, 2H, C$\underline{H}_2$—NH), 6.36, 6.39 and 7.35 in each case (m, 1-furan-H), 6.76 (s, 1H, 3-H), 6.86 (s, 1H, 7-H), 7.91 (s, 1H, 10-H), 9.09 (s, 1H, CHO).

C$_{21}$H$_{20}$N$_2$O$_5$ (380.40) Calculated: C. 66.28, H. 5.30, N. 7.40, Found: 66.11, 5.30, 7.28.

Example 7

1-Formyl-5,6-dihydro-8,9-dimethoxy-pyrrolo[2,1-a]isoquinoline-2-carboxylic acid-(2-methoxyethyl)-amide Prepared by rearrangement of 3-[3,4-dihydro-6,7-dimethoxyisoquinoline-(1)]-furan-4-carboxylic acid-(2-methoxyethyl)-amide hydrochloride with 2-methoxyethylamine (reaction time: 16 hours).

Yield: 78%; melting point: 142°–145° C. (ethylacetate/petroleum ether).

IR: 3240 w, 3200 m (NH), 3140 m, 3075 m, 1740 m (CO), 1640 s (CONH), 1580 s, 1530 s cm$^{-1}$.

$^1$H-NMR (CDCl$_3$): δ=3.02 (t, J=6.5 Hz; 2H, Ar—C$\underline{H}_2$), 3.44 (s, 3H, OCH$_3$), 3.61, 3.64 in each case (s, 2H, N$\underline{H}$—CH$_2$—CH$_2$—O), 3.93, 3.96 in each case (s, 3H, OCH$_3$), 4.04 (t, J=6.5 Hz; 2H, CH$_2$—C$\underline{H}_2$—N), 6.83 (s, 1H, 3-H), 7.07 (s, 1H, 7-H), 7.56 (s, 1H, 10-H), 10.13 (s, 1H, CHO).

MS: m/z=358 (20.5% M+), 330 (72%, M—CO), 300 (9.6%, M—CH=CH—OCH3), 284 (41%, M—NHCH2CH2OCH3), 256 (22.9%, 284-CO).

$C_{19}H_{22}N_2O_5$ (358.40) Calculated: C. 63.67, H. 6.19, N. 7.82; Found: 63.65, 6.46, 7.72.

Example 8

1-Formyl-5,6-dihydro-8,9-dimethoxy-pyrrolo[2,1-a]isoquinoline-2-carboxylic acid-[2-(3,4-dimethoxyphenyl)-ethyl]-amide Prepared by rearrangement of 3-[3,4-dihydro-6,7-dimethoxyisoquinolyl-(1)]-furan-4-carboxylic acid-[2-(3,4-dimethoxyphenyl)-ethyl]-amide-hydrochloride with piperidine.

Yield: 1.6 gm (68%) of reddish orange crystals; melting point: 154°-155° C. (from ethyl acetate).

IR: 3400 br w, 1740 m (CHO), 1670 s (NHCO), 1650 s, 1570 s cm$^{-1}$.

$^1$H-NMR (CHCl3): δ=2.71-3.18 (m, 4H, 2×Ar—CH2), 3.78 (s, 9H, 3×OCH3), 3.92 (s, 3H, OCH3), 3.58-4.07 (m, 4H, 2×CH2—CH2—N), 6.60-6.87 (m, gH, 4 aromatics-H, 1 pyrrol-H, 1 NHCO), 7.53 (s, 1H, 10-H), 9.22 (s, 1H, CHO). MS: m/z=464 (68%, M+), 313 (100%, M—CH2C6H3(OCH3)2), 285 (36%, 313-CO).

$C_{26}H_{28}N_2O_6$ (464.54) Calculated: C. 67.22, H. 6.08, N. 6.03; Found: 67.32, 6.31, 6.19.

The following is an example of preparation of a compound of Formula X:

Example 9

3,4-Dihydro-6,7-dimethoxy-12-(2-N,N-dimethylaminoethyl)-aminopyridazino[4',5':3,4]pyrrolo[2,1-a]isoquinoline hydrochloride

A.

3,4,11,12-Tetrahydro-6,7-dimethoxy-pyridazino[4',5':3,4]pyrrolo[2,1-a]isoquinolin-12-one A mixture of 8.25 gm of ethyl-1-formyl-5,6-dihydro-8,9-dimethoxy-pyrrolo[2,1-a]isoquinolin-2-carboxylate and 7 ml of hydrazine hydrate in 40 ml pyridine was stirred for three hours at boiling temperature. After cooling, the crystalline precipitate was removed and washed with methanol to remove any remaining pyridine. The resulting product was found by analysis to be pure and was used in the following step without further purification.

Yield: 7.1 gm (95.4% of theory), M.p.: >285° C.

B.

3,4,11,12-Tetrahydro-6,7-dimethoxy-pyridazino[4',5':3,4]pyrrolo[2,1-a]isoquinolin-12-thione Three hundred two grams of phosphorpentasulfide were added quickly in a number of portions to a suspension of 404 gm of the compound obtained in Step A in 2.8 liters of pyridine under stirring at room temperature. When the temperature was raised slightly (maximum 60° C.), a yellow solution formed, from which orangish yellow crystals precipitated after a short time. The reaction mixture was then heated at reflux for about four hours and allowed to cool to room temperature, and the crystals were filtered under reduced pressure. The crystals were then dispersed in a mixture of 1 liter of water and 200 ml of methanol, and after filtration under reduced pressure, the crystals were dried under vacuum at 60° C.

The resulting product was used in the following step without further purification.

Yield: 392 gm (92% of theory), M.p.: 294° C.

C.

3,4-Dihydro-6,7-dimethoxy-12-methylmercaptopyridazino-[4',5':3,4]pyrrolo[2,1-a]isoquinoline Twenty milliliters of methyliodide were added to a suspension of 100 gm of 3,4,11,12-tetrahydro-6,7-dimethoxy-pyridazino[4',5':3,4]pyrrolo[2,1-a]iosquinolin-12-thione in 600 ml of dimethylacetamide at room temperature under stirring. After about 20 minutes of stirring at room temperature, an orange solution formed, from which orange crystals precipitated. Stirring was continued for a further hour, and the resulting crystals were then filtered under reduced pressure and washed with methylene chloride. A second fraction was obtained by evaporation of the mother liquor and grinding of the crystals in methylene chloride, followed by removal of the methylene chloride. By NMR analysis the product was found to be pure.

Yield: 99.8 gm (96% of theory), M.p.: 254° C.

D.

3,4-Dihydro-6,7-dimethoxy-12-(2-N,N-dimethylaminoethyl)amino-pyridazino[4',5':3,4]pyrrolo[2,1-a]isoquinoline hydrochloride Eight grams of 3,4-dihydro-6,7-dimethoxy-12-methylmercapto-pyridazino[4',5':3,4]pyrrolo[2,1-a]isoquinoline and 15 ml of 2-(N,N-dimethylaminoethyl)-amine were heated for two hours in 100 ml of dimethylacetamide at boiling temperature. Upon cooling to room temperature, the resulting orange solution was concentrated by evaporation of the solvent under reduced pressure, and the oily residue was dissolved in methylene chloride, extracted with water, and dried over sodium sulfate.

After removal of the solvents, the solids were purified in an Al2O3-column [Al2O3 neutral, Woelm, Activity grade III; eluant: methylene chloride/methanol (100:8)]. The reaction product was dissolved in ethanol and reprecipitated as the hydrochloride by the addition of ethanolic hydrochloric acid.

Yield: 6.6 gm (73% of theory), M.p.: >250° C.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process of preparing a compound of the formula

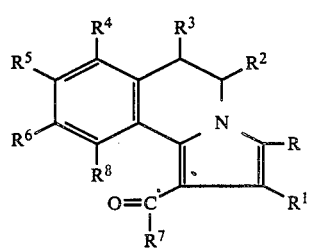

wherein
R, $R^2$, $R^3$, and $R^7$ are each independently hydrogen or alkyl of 1 to 4 carbon atoms;

$R^1$ is cyano, hydroxycarbonyl, (alkoxy of 1 to 4 carbon atoms)carbonyl, (hydroxy-lower alkyl)aminocarbonyl, furfuryl-aminocarbonyl, (lower alkoxy-lower alkyl)aminocarbonyl, (lower alkoxy-phenyl)-lower alkylaminocarbonyl or (di-lower alkoxy-phenyl) lower alkyl-aminocarbonyl;

$R^4$ and $R^8$ are each independently hydrogen, hydroxyl, alkoxy of 1 to 4 carbon atoms, (alkyl of 1 to 4 carbon atoms)thio or $-NR^9R^{10}$;

$R^5$ and $R^6$ are each independently hydroxyl, alkoxy of 1 to 4 carbon atoms or (alkyl of 1 to 4 carbon atoms)thio; or $R^5$ and $R^6$, together with each other, are $-O-CH_2-O-$, $-O-CH_2-CH_2-O-$ or $-O-CH=CH-O-$;

$R^9$ is hydrogen or alkyl of 1 to 4 carbon atoms; and $R^{10}$ is alkyl of 1 to 4 carbon atoms, hydroxy(alkyl of 1 to 4 carbon atoms), methoxy(alkyl of 1 to 4 carbon atoms) or furfuryl (alkyl of 1 to 4 carbon atoms), which comprises heating a 1-(3-furyl)-3,4-dihydroisoquinoline of the formula

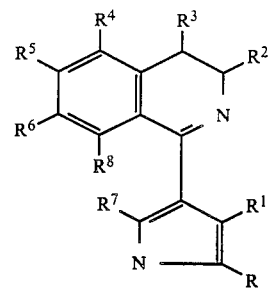

wherein R, $R^1$, $R^2$, $R^3$, $R^4$, $R^5$, $R^6$, $R^7$ and $R^8$ have the meanings defined above, in the presence of a primary or secondary aliphatic, cycloaliphatic or araliphatic amine at a temperature of between 80° C. and the boiling point of the reaction mixture for several hours, removing the amine from the reaction mixture, treating the residue with a dilute acid, and isolating the reaction product.

2. A process of claim 1, where said amine is morpholine, piperidine, 2-(3,4-dimethoxyphenyl)-ethylamine, 1-amino-2-propanol or methoxy-ethylamine.

3. A process of claim 1, where said dilute acid is a dilute inorganic acid.

4. A process of claim 1, where said dilute acid is dilute hydrochloric acid.

* * * * *

UNITED STATES PATENT AND TRADEMARK OFFICE
CERTIFICATE OF CORRECTION

PATENT NO. : 4,766,217  
DATED : August 23, 1988  
INVENTOR(S) : Walter Lösel et al Page 1 of 5

It is certified that error appears in the above-identified patent and that said Letters Patent is hereby corrected as shown below:

Cover page, insert --[30] Foreign Application Priority Data  
        Jan. 13, 1984 [DE] Fed. Rep. of  
        Germany .... 3401018--

Abstract, line 30

"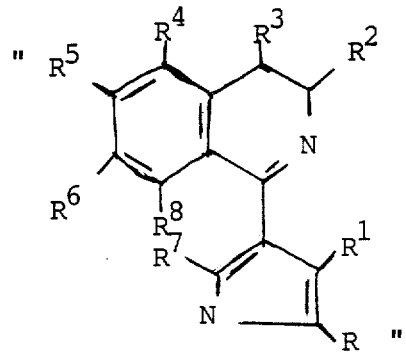"

should read

--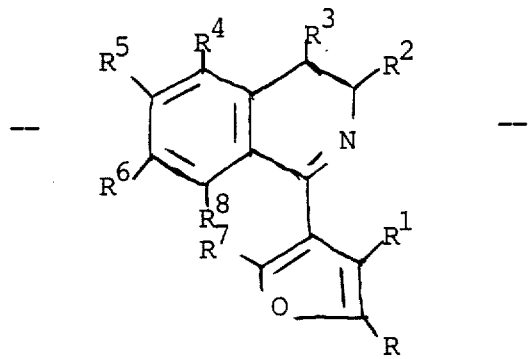--

UNITED STATES PATENT AND TRADEMARK OFFICE
CERTIFICATE OF CORRECTION

PATENT NO. : 4,766,217
DATED : August 23, 1988
INVENTOR(S) : Walter Lösel et al

It is certified that error appears in the above-identified patent and that said Letters Patent is hereby corrected as shown below:

Column 2, line 10

"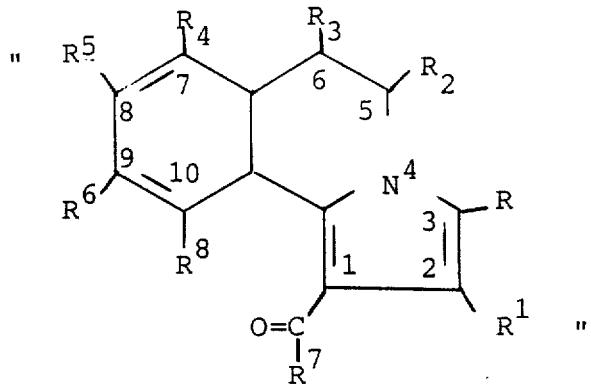"

should read

--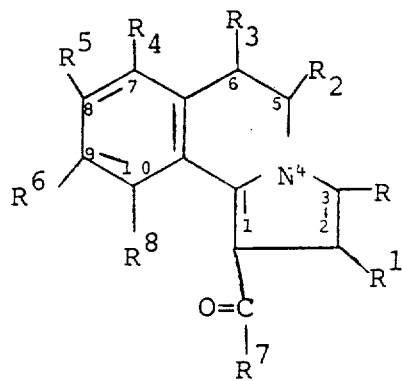--

UNITED STATES PATENT AND TRADEMARK OFFICE
CERTIFICATE OF CORRECTION

PATENT NO. : 4,766,217

DATED : August 23, 1988

INVENTOR(S) : Walter Lösel et al

It is certified that error appears in the above-identified patent and that said Letters Patent is hereby corrected as shown below:

Column 4, lines 1-10 "

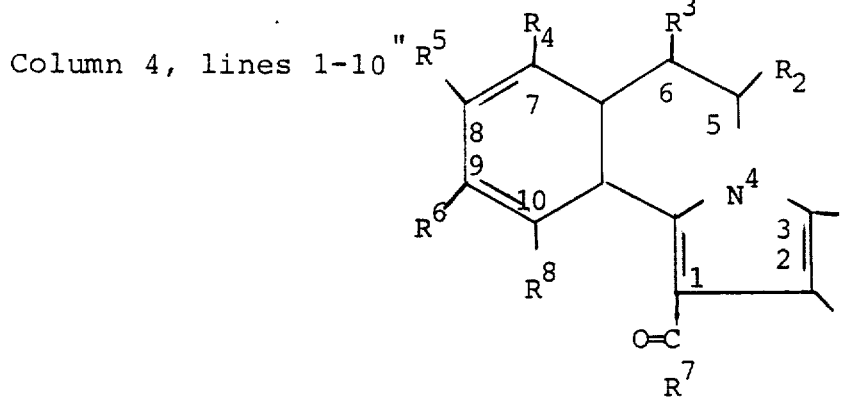

should read

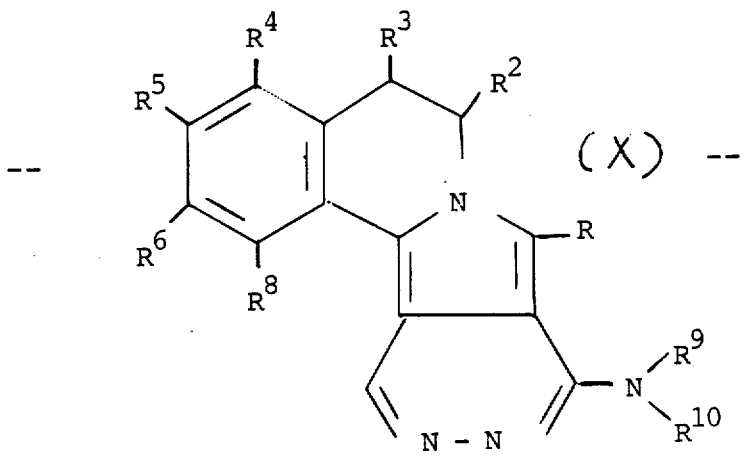  (X) --

UNITED STATES PATENT AND TRADEMARK OFFICE
CERTIFICATE OF CORRECTION

PATENT NO. : 4,766,217

DATED : August 23, 1988

INVENTOR(S) : Walter Lösel et al

It is certified that error appears in the above-identified patent and that said Letters Patent is hereby corrected as shown below:

Column 5, line 11, "pyridazinio" should read --pyridazino--.

Column 9, line 35, "67 = 1.36" should read --$\delta$= 1.36--.

Column 10, line 41, "67 = 2.89: should read --$\delta$= 2.89--.

Column 14, line 14 "

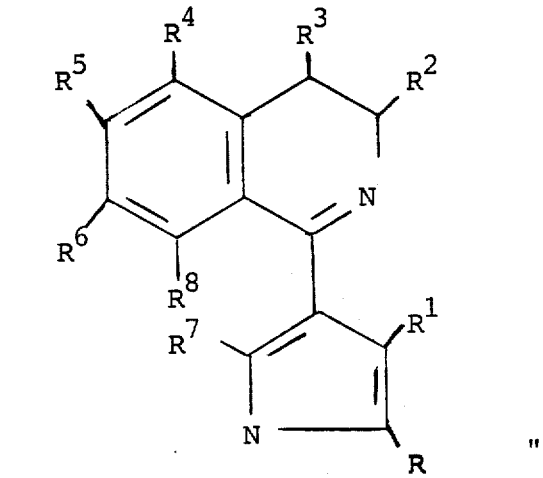

"

should read

UNITED STATES PATENT AND TRADEMARK OFFICE
CERTIFICATE OF CORRECTION

PATENT NO. : 4,766,217

DATED : August 23, 1988

INVENTOR(S) : Walter Lösel et al

Page 5 of 5

It is certified that error appears in the above-identified patent and that said Letters Patent is hereby corrected as shown below:

-- 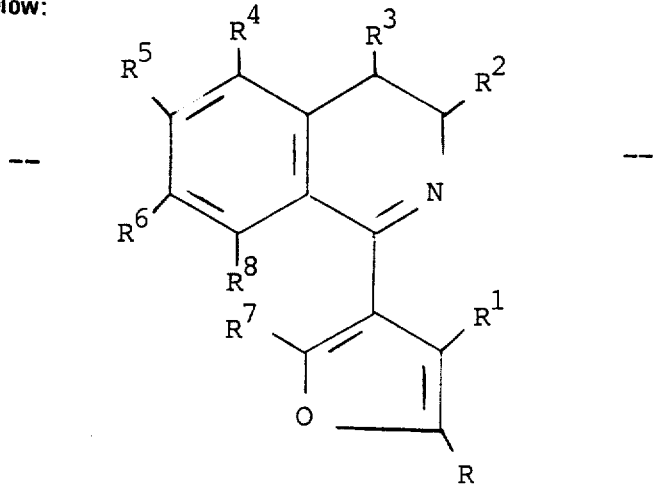 --

Signed and Sealed this

Twenty-fourth Day of December, 1991

Attest:

HARRY F. MANBECK, JR.

*Attesting Officer*  *Commissioner of Patents and Trademarks*